United States Patent [19]

Ellis et al.

[11] 4,027,393

[45] June 7, 1977

[54] METHOD OF IN VIVO STERILIZATION OF SURGICAL IMPLANTABLES

[75] Inventors: Franklin H. Ellis; Stephen W. Andrews, both of Rochester, N.Y.

[73] Assignee: Sybron Corporation, Rochester, N.Y.

[22] Filed: Sept. 19, 1975

[21] Appl. No.: 614,911

[52] U.S. Cl. .............................. 32/10 A; 32/40 R; 32/1; 128/172.1
[51] Int. Cl.² ........................................ A61C 13/00
[58] Field of Search ............. 32/10 A, 40 R, 1, 57, 32/15; 128/303 R, 172.1

[56] References Cited

UNITED STATES PATENTS

| 2,121,875 | 6/1938 | Kruse et al. | 32/1 X |
| 2,276,623 | 3/1942 | Meiman | 32/1 |

Primary Examiner—G.E. McNeill
Assistant Examiner—Robert F. Cutting
Attorney, Agent, or Firm—Theodore B. Roessel; J. Stephen Yeo

[57] ABSTRACT

Surgical and dental apparatus may be sterilized after implantation in the patient and caused to provide bactericidal effects in the tissue proximate to the apparatus. The apparatus contains silver or is silver coated. A positive current is applied to the apparatus which releases atomic silver into the volume surrounding the apparatus.

2 Claims, 5 Drawing Figures

METHOD OF IN VIVO STERILIZATION OF SURGICAL IMPLANTABLES

BACKGROUND OF THE INVENTION

This invention relates to surgical instruments and more specifically concerns the sterilization of surgical implantables in vivo by electrical means.

Any time an incision is made in the body there is the possibility of infection due to pathogenic microorganisms entering through the incision. If an appliance or a device is implanted there is also the possibility of such microorganisms being present on the appliance or device.

It is known that the healing of various skin lesions and ulcers may be accelerated by electrotherapy techniques involving the application of low intensity direct current through electrodes attached to the area adjacent to the pathologic tissue. In a copending U.S. application, Ser. No. 545,609, filed Jan. 30, 1975 by your applicants, it is disclosed that the use of silver or silver bearing material in the construction of the positive electrode further aids the healing process by providing a bactericidal effect. One explanation of this effect is that positive silver ions are formed which chemically bind with the DNA molecules of the bacteria and prevent reproduction thereof.

Apparatus disclosed in Ser. No. 545,609 provides current to promote tissue growth, while bactericidal action is a desirable secondary effect.

Many surgical and dental devices are normally electrically passive. It is desirable during use to provide bactericidal action on the device and in the tissue about the implantation site of the device. In U.S. Pat. No. 2,121,875 by W. Kruse et al., there is taught a process for sterilizing and disinfecting water, surgical instruments, root canals of teeth and catheters. A silver bearing electrode is used as an anode in a direct current path. Kruse calls for pretreating the anode so that it is coated with silver compounds before use. A high current density is also called for, the total current being in the milliampere range for treating the electrode during sterilization of a root canal.

In contrast, the present invention calls for low current to be continuously applied to an electrode so as to liberate silver ions from the electrode.

SUMMARY OF THE INVENTION

A method is provided to sterilize silver containing surgical and dental apparatus after insertion or implantation in a patient. The method will also yield bactericidal treatment of tissue proximate to the apparatus.

The apparatus is supplied with positive current at the rate of approximately one microampere per square centimeter of apparatus surface area. The method may be directed to catheters whereupon the catheter may contain silver or a silver electrode small enough for insertion through said catheter is provided.

The invention may also be used for the sterilization of root canals. A silver post is inserted into the root canal and one-half to two microamperes of positive current is applied for approximately one-half hour.

DESCRIPTON OF THE INVENTION

This invention provides a method of killing bacteria on surgical appliances or devices after implantation and, to a certain extent, killing other microorganisms which may enter the incision. It supplements conventional sterilization and provides added assurance that a deep seated infection will not occur post-operatively.

The bactericidal effect is achieved by the use of silver and small electric currents in the range of 0.1 to 40 microamperes. Laboratory tests have verified that silver electrodes have a bactericidal effect at currents of one tenth the magnitude necessary when other electrode materials such as platinum, gold, stainless steel, and copper are used. Bacteria tested were those normally found in wounds such as Pseudomonas Aeruginosa, Proteus Vulgaris, Staphyloccus Aureus and Escherichia Coli.

This invention is applicable to the sterilization of a number of silver containing surgical appliances including orthopedic and dental fixation appliances such as bone screws, plates, nails, pins and prostheses, and dental blade implants for fixing dentures to alveolar bone as well as metal suture wire and neurosurgical clips.

Figure 1:
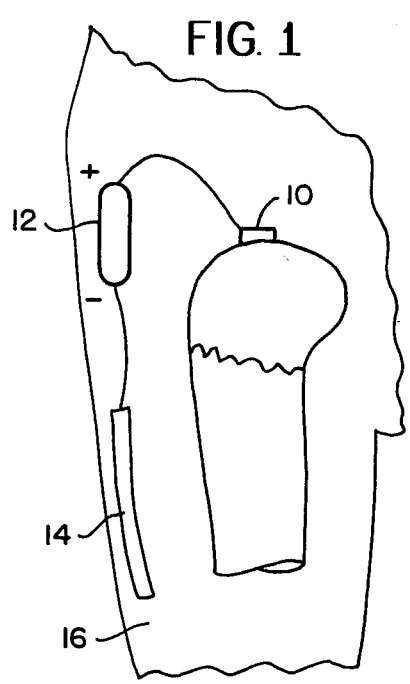
FIG. 1 is a diagram of an arrangement for sterilizing surgical appliances in keeping with the teachings of the invention.

The surgical appliance does not have to be totally constructed of silver, but may be made of stainless steel or other material which is silver coated. In FIG. 1, a nail 10 is illustrated as an example of a surgical appliance.

In practicing the invention the beneficial effects of silver and small electrical currents are obtained by using a silver or silver plated appliance 10 as the positive electrode of a known constant current generator 12. The negative electrode 14 can be a silver wire or plate preferably having surface area equal to or greater than that of the appliance. It is placed in soft tissue 16 a short distance from the appliance 10. The current is set at a level equal to approximately one microampere per square centimeter of appliance surface area. Since, in most cases the appliance is to be left implanted for a long period of time, the generator, negative electrode and connecting wires are arranged at the time of implantation to facilitate their removal in 3 to 6 weeks.

If the appliance is to be plated, the minimum amount of silver plated onto the appliance has been determined empirically to be that required to produce 7 micrograms per millimeter of treated volume. Since the maximum penetration observed with regularity is about 5 millimeters, the thickness of the plating works out to be about $10^{-7}$ inches of silver. In actual practice, about 1 to 10 microinches of silver is deposited on the appliance by sputtering. Sputtering is a known high vacuum deposition process which produces thin, high purity silver film with superior adhesion.

The silver plating on the appliance is sufficient to produce 10 to 100 times as much silver in the tissue in the area as is necessary to achieve a total bactericidal effect. This is because experimental tests have indicated that silver is attracted to protein and other materials in a living system, so that these materials become bound to the positive electrode. These tests indicate that even when sufficient silver is available for 100 times the required 7 micrograms per milliliter, only the 7 micrograms actually can be detected spectrographically in the tissue. The direct current used can be applied continuously or periodically at intervals of one to four hours for periods of five to thirty minutes. The current causes silver ions to be passed from the surface of the electrode into the tissue fluid at a rate of about 0.00112 grams per second.

Figure 2:
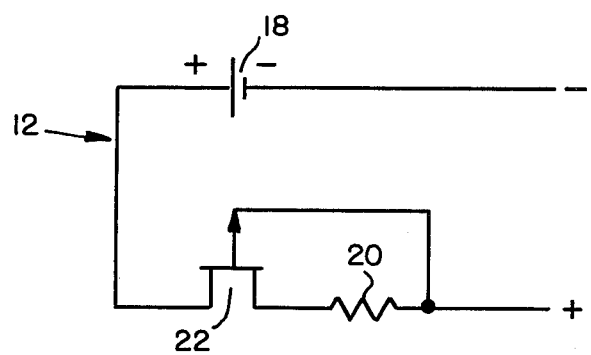
FIG. 2 is a schematic of a known constant current generator suitable for practicing the invention.

In the above and following examples of the invention, the direct current may be supplied by a constant current generator. FIG. 2 is a schematic of a simple battery operated generator suitable for practicing the invention. The circuitry is well known and will only be briefly described.

The battery 18 may be a 1.35 volt mercury cell of the long life variety such as a Mallory WH1T2. The controlled current flows through resistor 20 establishing a bias voltage between the source and gate of a field effect transistor 22. When the bias voltage reaches a level so as to bias transistor to pass current sufficient to produce an equal voltage across resistor 20 the curcuit becomes a constant source due to the known characteristics of a field effect transistor. As shown in FIG. 1 the negative terminal of the battery connects to an electrode in electrical communication with soft tissue near the appliance. Resistor 20 is electrically connected to the appliance via a length of insulated wire.

A second application of the invention is the sterilization of root canals during endodontic procedures.

Typical root canal therapy is aimed at saving teeth with pulpal involvement by debridement, sterilization and obturation. Debridement is accomplished by filing away the defective pulp. Obturation is accomplished by filling the root canal with a post of the appropriate size to fill the space left by filing. This post has been made of gold, silver, gutta percha, etc. The difficult part of the process is sterilization of the canal. Liquid sterilants can often force infected material into the apex of the canal where an abcess can form, or an abcess may already be present.

Figure 3:
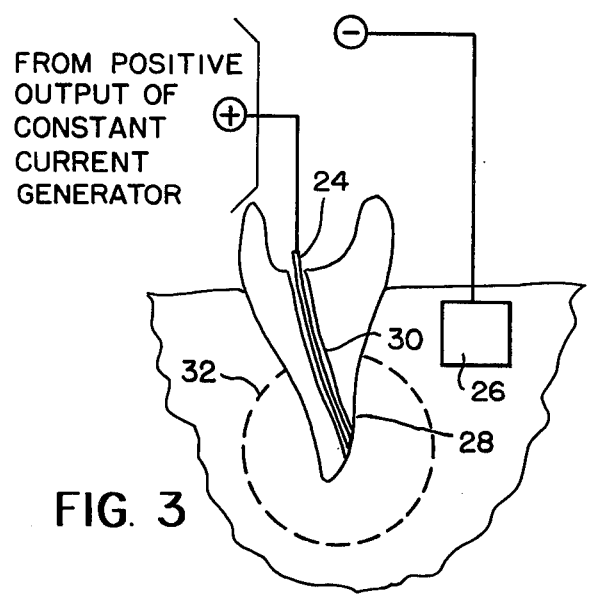
FIG. 3 represents the sterilization of a root canal following the invention.

Referring to FIG. 3, a post 24 containing silver is used as a positive anode electrode in combination with the circuit 12 of FIG. 2 and a negative plate 26. The tooth is prepared in a conventional manner. The anode electrode is placed in the tooth 28 extending to the bottom of the root canal 30. A current of one-half to two microamperes for approximately one-half hour releases enough silver ions to insure a sterile canal. The sterile area will extend radially approximately one-half centimeter in all directions from such a post due to the concentration of silver ions in the pulpal material. This will penetrate tubules in the pulp and extend into the apical area 32 one-half centimeter beyond the end of the post 24. In vitro testing has shown this technique to be an effective bactericidal mechanism for Streptococcus Mutans, Streptoccus Mitis, Streptococcus Salivarius, Enterobacter Aerogenes, Escherichia Coli, Staphylococcus Aureus and other bacteria found in infected root canals.

The post may be allowed to remain in the canal to seal it.

Following the above teachings will allow the obtaining of complete sterility so that dental procedure may be completed in a single appointment by the dentist.

Yet another application of the invention is the sterilization of indwelling catheters. Any catheter that is in place for an extended period of time presents a path for bacterial invasion.

Figure 4:
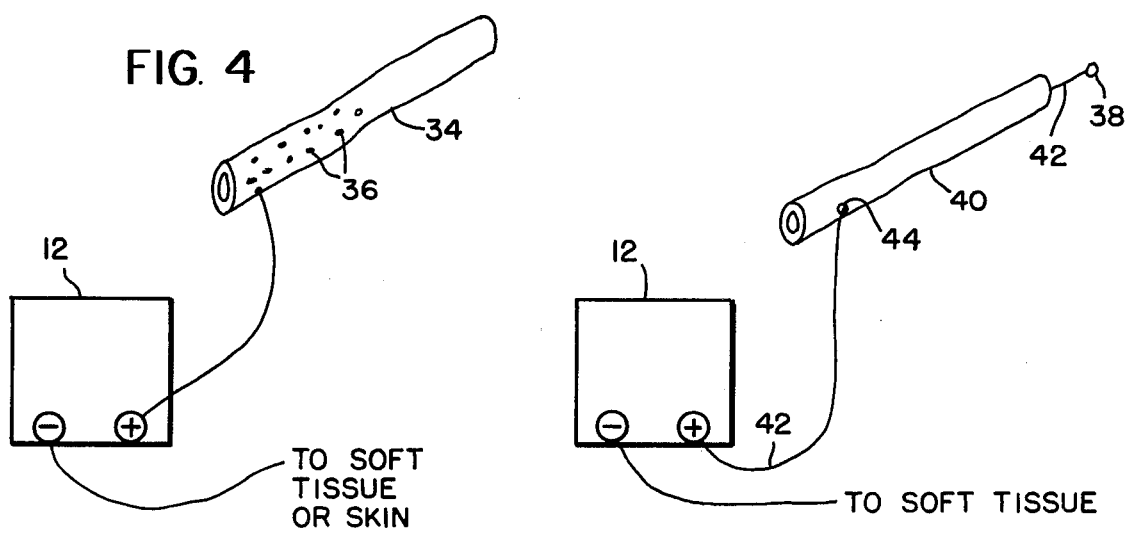
FIGS. 4 and 5 are examples of the invention embodied as catheters.
Figure 5:
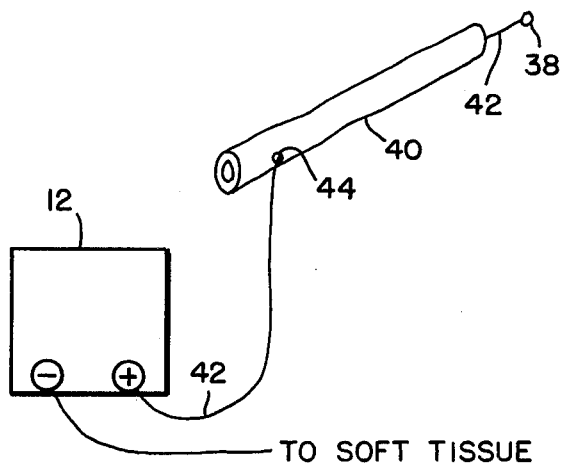

An electrode to control or eliminate infection may be formed as part of the catheter 34 represented by FIG. 4. During manufacture silver particles 36 are suspended in the catheter wall which may be an elastomer tube.

During the time the catheter is indwelling, current flow is applied having a magnitude so that the voltage appearing between electrodes stays below one volt. Positive potential is applied to the conductive catheter which acts as an anode, while a negative electrode is placed in the effluent or on the patient's skin. This procedure provides continuous liberation of silver ions into effluent in the catheter and silver ion availability on the outer surface.

Alternatively, the anode electrode may take the form of a flag or umbrella-shaped positive electrode 38 temporarily attached to a non-conductive catheter 40 with glucose or some other soluble adhesive. This electrode would then deploy into the residual urine which remains in the bladder. Electrical connection is made to the electrode by means of an insulated wire 42 located inside the catheter 40 and passing through the catheter wall at the distal end 44. Current is periodically applied. Normal flow of urine into the bladder combined with movement of the patient will provide a mixing action to cause evolved silver ions to be dispersed through the urine.

A laboratory simulation of a catheterized bladder was modeled using a 125 ml boiling flask as a "bladder". 50 ml of sterile culture medium were "infected" with a heavy culture of E. Aerogenes. 20 uA of positive current applied through a silver electrode kept the bacterial concentration at the level of original infection or less, as measured by optical density. For 3–4 hours after current was removed the treated fluid remained clear. After overnight incubation, infection virtually matched the control.

We claim:

1. A method to sterilize exposed root canals of teeth during endodontic procedures, comprising of the steps of:
   inserting a silver post into the root canal to the tip of said root canal; and
   applying positive current to said post at a level of approximately one-half to two microamperes for a time sufficient to affect sterilization.

2. A method according to claim 1 wherein said time is approximately one-half hour.

* * * * *